(12) United States Patent
Kim et al.

(10) Patent No.: US 7,745,177 B2
(45) Date of Patent: Jun. 29, 2010

(54) METHOD FOR MANUFACTURING XYLITOL WITH HIGH-YIELD AND HIGH-PRODUCTIVITY

(75) Inventors: Jung-Hoe Kim, Taejon (KR); Byoung-Sam Ko, Gwangju (KR)

(73) Assignees: Korea Advanced Institute of Science and Technology (KR); LPBIO Co., Ltd., Seoul (KR)

( * ) Notice: Subject to any disclaimer, the term of this patent is extended or adjusted under 35 U.S.C. 154(b) by 0 days.

(21) Appl. No.: 11/677,685

(22) Filed: Feb. 22, 2007

(65) Prior Publication Data

US 2008/0206821 A1    Aug. 28, 2008

(51) Int. Cl.
| | |
|---|---|
| C12P 19/00 | (2006.01) |
| C12N 9/00 | (2006.01) |
| C12N 9/02 | (2006.01) |
| C12N 1/20 | (2006.01) |
| C12N 15/00 | (2006.01) |
| C07H 21/04 | (2006.01) |

(52) U.S. Cl. ............... 435/72; 435/183; 435/189; 435/252.3; 435/254.11; 435/254.22; 536/23.2

(58) Field of Classification Search ............ 435/183, 435/189, 252.3, 254.11, 254.22, 320.1; 536/23.2
See application file for complete search history.

(56) References Cited

U.S. PATENT DOCUMENTS 5,686,277 A    11/1997   Kim et al. ............... 435/158
5,998,181 A    12/1999   Kim et al. ............... 435/158

OTHER PUBLICATIONS

Ko et al. Biotechnol Lett. Aug. 2006;28(15):1159-62. Epub Jun. 30, 2006.*
Ko et al. Appl Environ Microbiol. Jun. 2006;72(6):4207-13.*
Jeffries et al., "Metabolic engineering for improved fermentation of pentoses by yeasts" Appl. Microbiol. Biotechnol. 63:495-509, 2004.
Kim et al., "Improvement of Xylitol Production by Controlling Oxygen Supply in Candida parapsilosis" J. of Fermentation & Bioengin. 83(3):267-270, 1997.
Ko et al., "Production of Xylitol from D-Xylose by a Xylitol Dehydrogenase Gene-Disrupted . . . " Appl. & Environ. Microbiol. 72(6):4207-4213, 2006.
Ko et al., "Enhancement of xylitol productivity and yield using a xylitol dehydrogenase gene-disrupted mutant . . . " Biotechnol. Lett. 28:1159-1162, 2006.
Kotter et al., "Isolation and Characterization of the Pichis stipitis xylitol dehydrogenase gene . . . " Curr. Genet. 18:493-500, 1990.
Oh et al., "Increase of Xylitol Production Rate by Controlling Redox Potential in Candida parapsilosis" Biotech. & Bioengin. 58(4):440-444, 1998.
Parajo et al., "Biotechnological Production of Xylitol. Part 1: Interest of Xylitol and Fundamentals of its Biosynthesis" Bioresource Technol. 65:191-201, 1998.
Ko et al., "Molecular Cloning and Characterization of NAD$^+$-Dependent Xylitol Dehydrogenase . . . " Biotechnol. Prog. 22:1708-1714, 2006.

* cited by examiner

*Primary Examiner*—Christian L Fronda
(74) *Attorney, Agent, or Firm*—Fish & Richardson P.C.

(57) ABSTRACT

The present invention provides a method for manufacturing xylitol with high-yield and high-productivity by using a xylitol dehydrogenase-deficient mutant of xylitol producing microorganism. This goal is achieved through modification of the metabolic pathway of the xylitol producing microorganism, preferably a natural xylose-assimilating yeasts and fungi, by disrupting or inactivating the expression of desired genes.

7 Claims, 6 Drawing Sheets

METHOD FOR MANUFACTURING XYLITOL WITH HIGH-YIELD AND HIGH-PRODUCTIVITY

FIELD OF THE INVENTION

The present invention relates to a method for manufacturing xylitol with high-yield and high-productivity, more specifically, to a method for manufacturing xylitol with high-yield and high-productivity using a xylitol dehydrogenase-deficient mutant of xylitol producing microorganism.

BACKGROUND OF THE INVENTION

Xylitol, a five-carbon sugar alcohol, is used as a natural sweetener in the food and confectionary industry. It has an anticariogenic effect that inhibits the growth of the tooth-decaying bacterium *Streptococcus mutans* (see: Mäkinen, K. K., *J. Appl. Nutr.*, 44:16-28 (1992)). Its sweetness level is equal to that of sucrose, and it can replace sucrose on a weight-to-weight basis. When dissolved in water, xylitol has low viscosity and negative heat effects, and it does not require insulin for metabolic regulation. Owing to these benefits, the use of xylitol in the food industry is growing rapidly.

On a large-scale, xylitol is currently produced by chemical reduction of D-xylose derived mainly from wood hydrolysates. D-Xylose is a major pentose sugar found in lignocellulose and the second most abundant natural sugar (see: Ladisch, M. R., et al., *Enzyme Microb. Technol.*, 5:82-102 (1983)). The conventional process of xylitol production includes four steps: acid hydrolysis of plant material, purification of the hydrolysate to pure D-xylose, hydrogenation of the D-xylose to xylitol, and crystallization of the xylitol (see: Aminoff, C., et al., In Counsell, J. N. (ed.). Xylitol. Applied Science Publishers, London, p. 1-9 (1978)). However, the purification of pure D-xylose is very expensive and pollutive step (see: Kind, V. B. et al., *Gidroliz. Lesokhim. Promst.*, 3:11-12 (1987)). In addition, the hydrogenation of the D-xylose to xylitol at high temperature and high pressure using Raney-nickel metal catalyst is dangerous and pollutive (see: Hyvönen, L., et al., In Advances in Food Research, Vol. 28, eds Chishester, C. O., Mrak, E. M. and Stewart, G., Academic Press, New York, pp. 373-403 (1982)).

The existing drawbacks of conventional xylitol production methods including high pollution levels and waste-treatment concerns motivated researchers to develop alternative ways for its production. One of the most attractive procedures is biological production. The biological production does not require high purity of the substrate, D-xylose, and is a safe and environmentally-friendly process. Xylitol is produced by natural xylose-assimilating yeasts and fungi, such as *Pachysolen tannophiulus, Candida guilliermondii, Candida parapsilosis*, and *Candida tropicalis* (see: Dahiya, J. S., *Can. J. Microbiol.*, 37:14-18 (1991), Yahashi, Y., et al., *J. Ferment. Bioeng.*, 81:148-152 (1996), Kim, S. Y., et al., *Food Sci. Biotechnol.*, 7:282-285 (1998), Morimoto, S., et al., *J. Ferment. Technol.*, 64:219-225 (1986)).

Although *Candida* sp. was reported to be the most active and thus potentially most useful strain, the industrial production of xylitol has yet to be achieved because of the high production costs associated with the substrate, D-xylose, an expensive raw material with a low yield of xylitol. Efforts to develop more cost-effective methods of production have included using controlling the dissolved oxygen (see: Kim, S. Y., et al., U.S. Pat. No. 5,686,277 (1997)). However, the controlling the dissolved oxygen at the level of 0.8-1.2% is not easy in the industrial scale and, as a result, the xylitol yield was below 70% and productivity could not achieve an economical efficiency.

To solve these problems, the construction of a novel xylitol production strain with high-yield and high-productivity using metabolic engineering has been continuously required in the art.

SUMMARY OF THE INVENTION

The present invention provides a method for manufacturing xylitol with high-yield and high-productivity by using a xylitol dehydrogenase-deficient mutant of xylitol producing microorganism. This goal is achieved through modification of the metabolic pathway of the xylitol producing microorganism, preferably a natural xylose-assimilating yeasts and fungi, by disrupting or inactivating the expression of desired genes.

A primary objective of the present invention is, therefore, to provide a method for manufacturing xylitol with high-yield and high-productivity by using a genetically modified microorganism whose xylitol dehydrogenase expression is disrupted by deletion, substitution, or addition of a part of the xylitol dehydrogenase gene.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

I. Genetic Modification of a Xylitol Producing Microorganism

The present invention provides a method for manufacturing xylitol which comprises a step of culturing a xylitol dehydrogenase-deficient mutant of xylitol producing microorganism whose xylitol dehydrogenase expression is disrupted by deletion, substitution or addition of a part of xylitol dehydrogenase gene in a medium containing xylose, carbon sources, nitrogen sources, and trace elements. In some instances the culturing continues until the xylose contained in the medium is substantially consumed. In some instances the culturing continues until the xylose in the medium is consumed completely. The xylitol producing microorganism includes natural xylose-assimilating yeasts and fingi, preferably of *Candida* sp. and more preferably using *Candida guillermodi*, *Candida parapsilosis*, or *Candida tropicalis*. Carbon sources, nitrogen sources, and trace elements are not specifically limited. In a preferred embodiment, glycerol, fructose, galactose, sucrose, mannose, maltose, cellobiose, or the mixture of these materials is used as carbon source for cell growth and cofactor regeneration for xylitol production, and yeast extract is used as nitrogen source, and potassium dihydrogenphosphate, magnesium sulfate heptahydrate, or the mixture of these materials is used as trace elements. In addition, fermentation condition for xylitol producing strain is not specifically limited. In a preferred embodiment, temperature for fermentation is ranged from 20° C. to 40° C.

Figure 1:
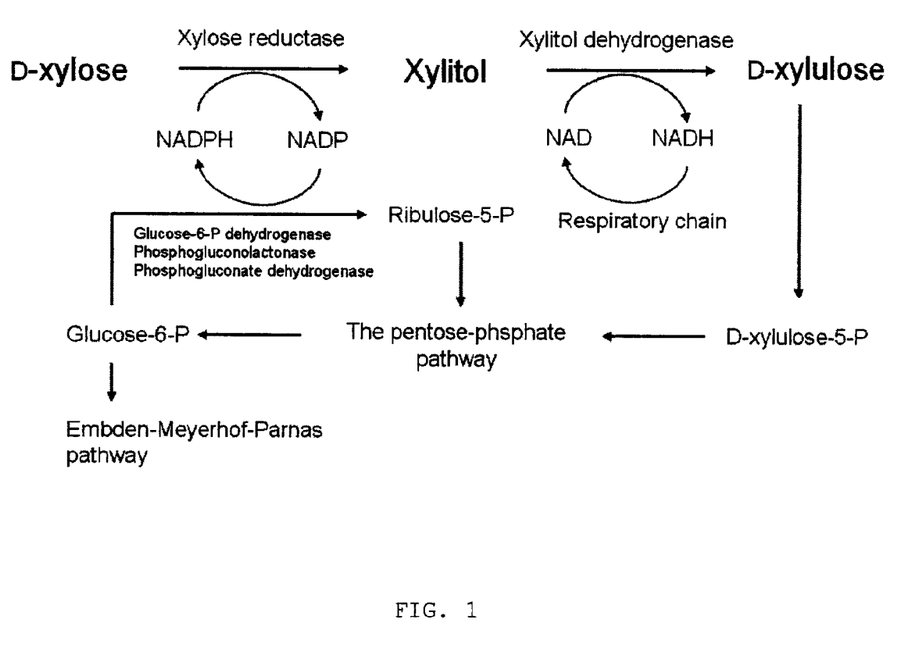
FIG. 1 is a schematic diagram of xylose metabolism in yeast.

More detailed description is as follows:

In general, xylitol is produced from xylose by xylose-assimilating yeasts and fungi in biological method for manufacturing xylitol. Most xylose-assimilating yeasts utilize D-xylose via two enzymatic oxidoreductive reactions with xylose reductase (EC 1.1.1.21) and xylitol dehydrogenase (EC 1.1.1.9) (see: Alexander, M. A., et al., *Appl. Microbiol. Biotechnol.*, 29:478-486 (1988)) as shown in FIG. 1. Xylose reductase catalyzes the reduction of D-xylose to xylitol, and xylitol dehydrogenase catalyzes the oxidation of xylitol to D-xylulose. D-Xylulose is converted to D-xylulose 5-phosphate by xylulose kinase and then enters the pentose phosphate pathway. Xylitol dehydrogenase requires NAD as a cofactor, whereas xylose reductase uses NAD(P)H. The overall efficiency of xylose assimilation is therefore coupled with the activities of xylose reductase and xylitol dehydrogenase. Xylose reductase and xylitol dehydrogenase in xylose-utilizing yeast, *Pichia stipitis*, are encoded by XYL1 and XYL2, respectively (see: Amore, R., et al., *Gene*, 109:89-97 (1991), Kötter, P., et al., *Curr. Genet.*, 18:493-500 (1990)).

The main yield-limiting factor of xylitol manufacturing from xylose is the consumption of xylitol for cell growth and maintenance. Therefore, if the metabolic step from xylitol to D-xylulose could be blocked by inactivating the corresponding enzyme, xylitol dehydrogenase, and if cosubstrates were supplied for cell growth and cofactor regeneration, the yield of xylitol should reach the theoretical level of 100%.

To analyze the DNA sequence of xylitol dehydrogenase gene, XYL2, the partial putative XYL2 gene was amplified from genomic DNA of *Candida tropicalis* by polymerase chain reaction (PCR) using the primers which were designed based on the sequence of the XYL2 gene in *Pichia stipitis*. The amplified DNA fragment was purified and inserted into pGEM-T Easy. The partial XYL2 gene was sequenced, and the complete nucleotide sequence was subsequently determined. Using the DNA sequence of XYL2 gene, the modified xylitol dehydrogenase gene which could not express the activity of the enzyme was constructed by deletion, substitution, or addition. Then, the gene disruption plasmid, pXYL2-Ura3, was constructed. The linear disruption DNA fragment, amplified using pXYL2-Ura3, was inserted into the host strain, *Candida tropicalis*, and the mutant of which xylitol dehydrogenase gene was inactivated by homologous recombination was selected.

II. Production of Xylitol

The xylitol production by the genetically modified strain was evaluated in 250-ml flask containing 50 ml xylitol fermentation medium. The xylitol fermentation medium consisted of D-xylose, glucose, yeast extract, potassium dihydrogenphosphate, and magnesium sulfate heptahydrate. The modified stain converted D-xylose to xylitol with 100% of yield. However, all D-xylose in the medium was not converted to xylitol, indicating that all of the D-xylose consumed by the modified strain was converted to xylitol and xylitol production was limited by the lack of a cofactor required by xylose reductase, because xylitol could not be further metabolized to regenerate the cofactor.

An additional carbon source, cosubstrate, was required for cofactor regeneration during xylitol production, and thus various carbon sources were screened for efficient xylitol production. Xylitol fermentation was performed in 250-ml flask containing 50 ml of xylitol fermentation medium and various cosubstrates. Although the cells grew best in a medium containing glucose as a cosubstrate, xylitol production was favorable when glycerol, fructose, galactose, sucrose, mannose, maltose, or cellobiose was used as cosubstrate. In special, all D-xylose in the medium was converted to xylitol when glycerol was used as a cosubstrate.

When the genetically modified mutant of *Candida tropicalis* was cultured batchwise using glycerol as a cosubstrate, D-xylose in the medium was consumed completely in about 48 hours and produced xylitol with 98.3% of yield and 0.97 g $l^{-1}$ $h^{-1}$ of volumetric productivity. However, in case of fed-batch culture, D-xylose in the medium was consumed in about 14-15 hours and produced xylitol with 97-100% of yield and 3.48 g $l^{-1}$ $h^{-1}$ of volumetric productivity. As a result, it was demonstrated that fed-batch culture was more efficient to produce xylitol than batch culture.

On the other hand, when the mutant of *Candida tropicalis* was cultured in a fed-batch under a condition of agitation speed 300 to 500 rpm and oxygen transfer rate (OTR) 10 to 42 mmol $O_2$ $l^{-1}$ $h^{-1}$, the xylitol productivity was varied in the range of from 1.4 to 3.5 g $l^{-1}$ $h^{-1}$ with no change in the xylitol yield. Particularly, the xylitol productivity was maximal at agitation speed of 500 rpm and oxygen transfer rate (OTR) of 42 mmol $O_2$ $l^{-1}$ $h^{-1}$. However, the xylitol productivity was not decreased considerably in case of fed-batch culture working under a condition of agitation speed 300 rpm and oxygen transfer rate (OTR) 42 mmol $O_2$ $l^{-1}$ $h^{-1}$. As a result, it could be concluded that agitation speed and oxygen transfer rate (OTR) affect the glycerol assimilation rate and consequently the xylitol production rate.

To produce xylitol in an economical way, the genetically modified mutant of *Candida tropicalis* was cultured in a fed-batch by using the hydrolysate of corn cob, a waste material containing a major component of xylose, which gave a xylitol yield similar to that of using pure D-xylose. Accordingly, it was found that the hydrolysate of corn cob, instead of D-xylose, could be used as a substrate to produce xylitol in a cost-effective manner.

The present invention is further illustrated by the following examples, which should not be taken to limit the scope of the invention.

Example 1

Construction of Xylitol Dehydrogenase-Deficient Mutant of Candida tropicalis C. tropicalis genomic DNA was prepared using a total DNA extraction kit. The partial XYL2 gene was amplified by polymerase chain reaction (PCR). The DNA sequences of the primers used are as follows:

```
Primer XYL2-F:
5'-aatggtcttgggtcacgaatcc-3'    (SEQ ID NO: 1)

Primer XYL2-R:
5'-gctctgaccaagtcgtaggcttc-3'   (SEQ ID NO: 2)
```

The resulting fragment was purified using a PCR product purification kit and then inserted into pGEM-T Easy vector (PROMEGA, USA). Then, two target sites for BamHI restriction enzyme were introduced at the both ends of XYL2 gene fragment cloned in pGEM-T Easy vector and the resulting plasmid was referred as pGEM-XYL2. A 1.2-kb URA3 gene was amplified by PCR with genomic DNA of C. tropicalis using primers Ura3-F and Ura3-R. The DNA sequences of the primers used were as follows:

```
Primer Ura3-F:
                                        (SEQ ID NO: 3)
5'-ggatccattctagatgatctggtttggattgttggag-3'

Primer Ura3-R:
                                        (SEQ ID NO: 4)
5'-ggatccatctcgagtcatgagaactaaactagcag-3'
```

Figure 2:
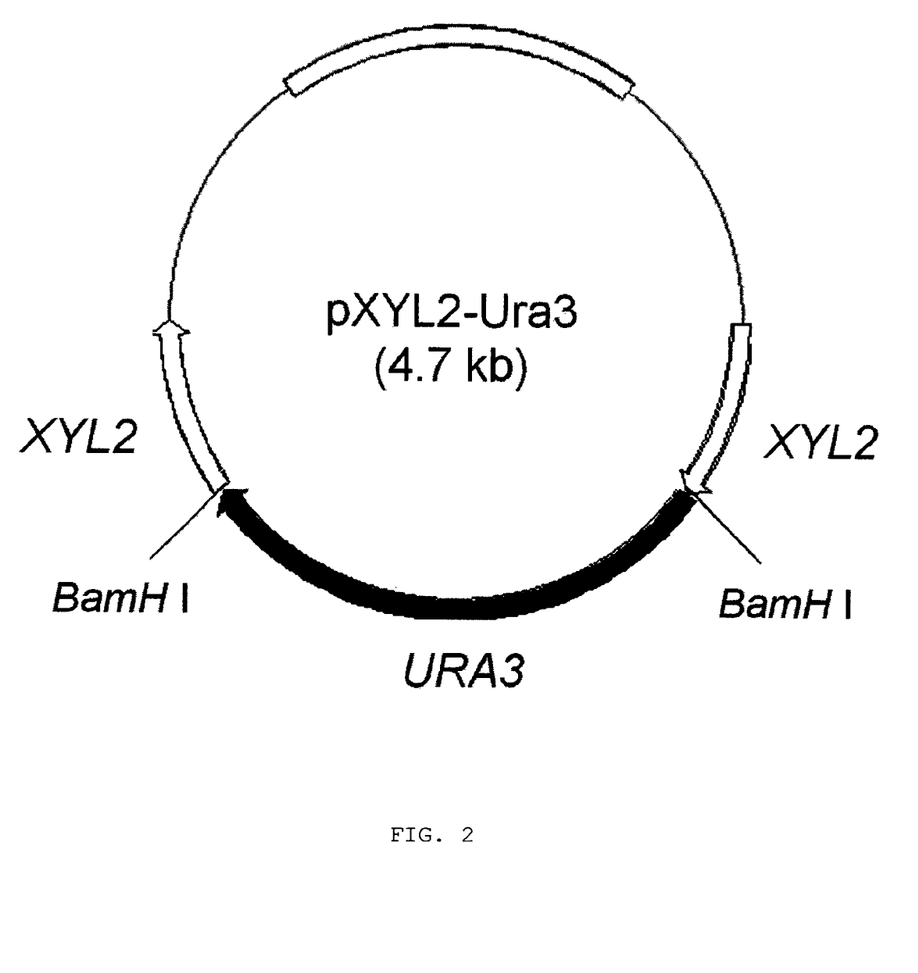
FIG. 2 is a restriction map of pXYL2-Ura3. The plasmid, pXYL2-Ura3, was used for the disruption of xylitol dehydrogenase gene of *Candida tropicalis*. Abbreviations: xyl2, xylitol dehydrogenase gene; ura3, orotidine-5'-phosphate decarboxylase gene.

The URA3 gene fragment amplified by PCR was inserted into pGEM-XYL2 to produce pXYL2-Ura3 as shown in FIG. 2. A linear DNA for transformation of C. tropicalis was amplified using PCR with the primer XYL2-F and XYL2-R. The resulting DNA fragment, XYL2-URA3-XYL2, was used as the disruption cassette. C. tropicalis was transformed using with the disruption cassette and selected on YNB plate (6.7 g l$^{-1}$ yeast nitrogen base without amino acid, 20 g l$^{-1}$ glucose, and 15 g l$^{-1}$ agar). The selected transformants were incubated on both YNB plate and xylose plate (6.7 g l$^{-1}$ yeast nitrogen base without amino acid, 20 g l$^{-1}$ D-xylose, and 15 g l$^{-1}$ agar) which contained D-xylose as a sole carbon source. The mutant which could grow on YNB and could not grow on xylose plate was selected, and the genetic modification of the selected mutant was confirmed by PCR. As a result, the xylitol dehydrogenase gene of the mutant (designated as 'BS-xdh') was successfully disrupted.

Example 2

Xylitol Production Using a Genetically Modified Strain

The modified strain, BS-xdh, which was constructed as described in Example 1 was inoculated in 15-ml test tube containing 3 ml of YM medium (3 g l$^{-1}$ yeast extract, 3 g l$^{-1}$ malt extract, 5 g l$^{-1}$ bactopeptone, and 20 g l$^{-1}$ glucose) and incubated using shaking incubator at 30° C. and 200 rpm for 12 hours. 1 ml of the said seed culture was inoculated in 250-ml flask containing 50 ml of xylitol production medium (50 g l$^{-1}$ D-xylose, 10 g l$^{-1}$ glucose, 10 g l$^{-1}$ yeast extract, 5 g l$^{-1}$ potassium dihydrogenphosphate, and 0.2 g l$^{-1}$ magnesium sulfate heptahydrate) and incubated using shaking incubator at 30° C. and 200 rpm for 36 hours. The samples (sample 1 to 7) were acquired every 6 hours.

Dry cell concentrations (dry cell weight per 1 L of culture), and concentrations of D-xylose, and xylitol of the sample 1 to 7 were analyzed, respectively. Dry cell weight was calculated from optical density of the sample using a spectrophotometer (Shimadzu, Japan) at 600 nm. The concentrations of D-xylose, xylitol, and various cosubstrates were analyzed by high pressure liquid chromatography (HPLC, Waters, USA) using a Sugar-Pak I column (Waters) with water as the mobile phase, at a column temperature of 90° C. and a flow rate of 0.5 ml min$^{-1}$. The results were shown in TABLE 1.

TABLE 1

Xylitol production profile using a xylitol production medium containing glucose as cosubstrate

| Sample | Culture time (hour) | Dry cell weight (gl$^{-1}$) | D-Xylose (gl$^{-1}$) | Xylitol (gl$^{-1}$) |
|---|---|---|---|---|
| 1 | 0 | 0.10 | 45.4 | 0.0 |
| 2 | 6 | 0.52 | 45.3 | 0.0 |
| 3 | 12 | 2.63 | 45.3 | 0.0 |
| 4 | 18 | 6.76 | 37.5 | 7.8 |
| 5 | 24 | 6.65 | 32.9 | 12.5 |
| 6 | 30 | 6.55 | 32.9 | 12.4 |
| 7 | 36 | 6.58 | 32.8 | 12.4 |

As shown in TABLE 1, the BS-xdh converted 12.5 g l$^{-1}$ of D-xylose to 12.5 g l$^{-1}$ of xylitol. The xylitol yield was 100%. However, D-xylose in the medium was not converted to xylitol anymore after 24 hours, and the production of xylitol stopped. The conversion ratio of D-xylose to xylitol was only 28%, and this result indicated that all of the D-xylose was not metabolized efficiently and that xylitol production was limited by the shortage of a cofactor required by xylose reductase.

Example 3

Screening of Cosubstrate for Cofactor Regeneration

The modified strain, BS-xdh, which was constructed as described in Example 1 was inoculated in 15-ml test tube containing 3 ml of YM medium (3 g l$^{-1}$ yeast extract, 3 g l$^{-1}$ malt extract, 5 g l$^{-1}$ bactopeptone, and 20 g l$^{-1}$ glucose) and incubated using shaking incubator at 30° C. and 200 rpm for 12 hours. 1 ml of the said seed culture was inoculated in 250-ml flasks containing 50 ml of various xylitol production media (50 g l$^{-1}$ D-xylose, 10 g l$^{-1}$ various carbon sources shown in TABLE 2 below, 10 g l$^{-1}$ yeast extract, 5 g l$^{-1}$ potassium dihydrogenphosphate, and 0.2 g l$^{-1}$ magnesium sulfate heptahydrate), and incubated using shaking incubator at 30° C. and 200 rpm for 96 hours.

After the end of fermentation, concentrations of produced dry cell (A), consumed various cosubstrates (B), consumed D-xylose (C), and produced xylitol (D) were measured as described previously. The D-xylose conversion ratio (E) was calculated from the consumed D-xylose concentration over initial D-xylose concentration in the medium and the production yield (F) was calculated from the produced xylitol concentration over the consumed D-xylose concentration. The results were shown in TABLE 2.

TABLE 2

Comparison of dry cell concentration(A), consumed cosubstrate(B),
consumed D-xylose(C), produced xylitol(D),
D-xylose conversion ratio(E), and xylitol yield(F)

| Carbon source | A(gl$^{-1}$) | B(gl$^{-1}$) | C(gl$^{-1}$) | D(gl$^{-1}$) | E(gl$^{-1}$) | F(gl$^{-1}$) |
|---|---|---|---|---|---|---|
| Mannose | 2.9 | 9.0 | 36.4 | 36.3 | 72.8 | 99.6 |
| Fructose | 5.3 | 8.9 | 23.3 | 23.6 | 46.6 | 101.2 |
| Galactose | 2.7 | 9.2 | 26.0 | 27.0 | 52.0 | 103.6 |
| Maltose | 2.2 | 8.3 | 29.9 | 27.2 | 59.8 | 90.9 |
| Sucrose | 4.4 | 8.9 | 35.5 | 36.0 | 71.0 | 101.3 |
| Lactose | 0.4 | 0.1 | 2.5 | 2.7 | 5.0 | 108.0 |
| Cellobiose | 3.5 | 9.1 | 39.4 | 38.3 | 78.8 | 97.2 |
| Meliobiose | 1.1 | 1.6 | 5.0 | 4.0 | 10.0 | 80.0 |
| Glycerol | 3.2 | 9.1 | 45.2 | 46.2 | 90.4 | 102.3 |
| Acetate | 1.0 | 9.0 | 11.0 | 12.3 | 22.0 | 112.1 |
| Gluconate | 1.0 | 2.1 | 3.9 | 4.0 | 7.8 | 102.2 |
| Propionate | 2.6 | 1.9 | 1.7 | 1.7 | 3.4 | 100.0 |
| Malate | 2.1 | 0.9 | 4.0 | 4.1 | 8.0 | 102.4 |

As shown in TABLE 2, when glycerol, fructose, galactose, sucrose, mannose, maltose, or cellobiose used as cosubstrate, above 90% of xylitol yield was achieved and the conversion ratios for these cosubstrates were higher than that for glucose (28%). In special, xylitol production was favorable when glycerol was the cosubstrate. When glycerol was used as cosubstrate, the production yield and D-xylose conversion ratio were 100% and 90%, respectively. Hence, glycerol was selected as the best cosubstrate for xylitol production.

Example 4

Xylitol Production Using Glycerol as Cosubstrate (I)

The modified strain, BS-xdh, which was constructed as described in Example 1 was inoculated in 15-ml test tube containing 3 ml of YM medium and incubated using shaking incubator at 30° C. and 200 rpm for 12 hours. 1 ml of the seed culture was inoculated in 250-ml flask containing 50 ml of xylitol production medium (50 g l$^{-1}$ D-xylose, 10 g l$^{-1}$ glycerol, 10 g l$^{-1}$ yeast extract, 5 g l$^{-1}$ potassium dihydrogenphosphate, and 0.2 g l$^{-1}$ magnesium sulfate heptahydrate) and incubated using shaking incubator at 30° C. and 200 rpm for 60 hours. The samples (sample 11 to 18) were acquired at 0, 6, 12, 18, 24, 36, 48 and 60 hours, respectively. Dry cell concentrations, and concentrations of D-xylose, glycerol, and xylitol were analyzed as described in Example 2. The results were shown in TABLE. 3.

TABLE 3

Xylitol production profile using a xylitol production medium
containing glycerol as cosubstrate

| Sample | Culture time (hour) | Dry cell weight (gl$^{-1}$) | Glycerol (gl$^{-1}$) | D-Xylose (gl$^{-1}$) | Xylitol (gl$^{-1}$) |
|---|---|---|---|---|---|
| 11 | 0 | 0.3 | 9.7 | 47.4 | 0.0 |
| 12 | 6 | 1.9 | 9.6 | 47.4 | 0.0 |
| 13 | 12 | 6.9 | 8.7 | 40.2 | 7.4 |
| 14 | 18 | 6.7 | 7.6 | 29.5 | 15.1 |
| 15 | 24 | 6.8 | 5.8 | 21.2 | 27.4 |
| 16 | 36 | 6.6 | 2.1 | 3.1 | 41.5 |
| 17 | 48 | 6.6 | 2.1 | 0.0 | 46.6 |
| 18 | 60 | 6.6 | 2.1 | 0.0 | 46.2 |

As shown in TABLE 3, the BS-xdh converted 47.4 g l$^{-1}$ of D-xylose to 46.6 g l$^{-1}$ of xylitol for 48 hours. All D-xylose in the medium was successfully converted to xylitol. This result indicated that the D-xylose was converted efficiently and xylitol was produced with sufficient supply of cofactor required by xylose reductase using glycerol as cosubstrate. In addition, the xylitol productivity and yield were 0.97 g l$^{-1}$ h$^{-1}$ and 98.3%, respectively.

Example 5

Xylitol Production Using Glycerol as Cosubstrate (II)

The modified strain, BS-xdh, which was constructed as described in Example 1 was inoculated in 15-ml test tube containing 3 ml of YM medium and incubated using shaking incubator at 30° C. and 200 rpm for 12 hours. 1 ml of the said seed culture was inoculated in 250-ml flask containing 50 ml of YM medium and incubated using shaking incubator at 30° C. and 200 rpm for 12 hours.

The 50 ml of the said seed culture was inoculated in a 2.5-liter jar fermenter (KoBiotech, Korea) containing 1 L of the xylitol production medium supplemented with 20 g l$^{-1}$ glycerol at pH 4.5, and 30° C. Dry cell weight, D-xylose, glycerol and xylitol concentrations were analyzed as described in Example 2. The results were shown in FIG. 3.

Figure 3:
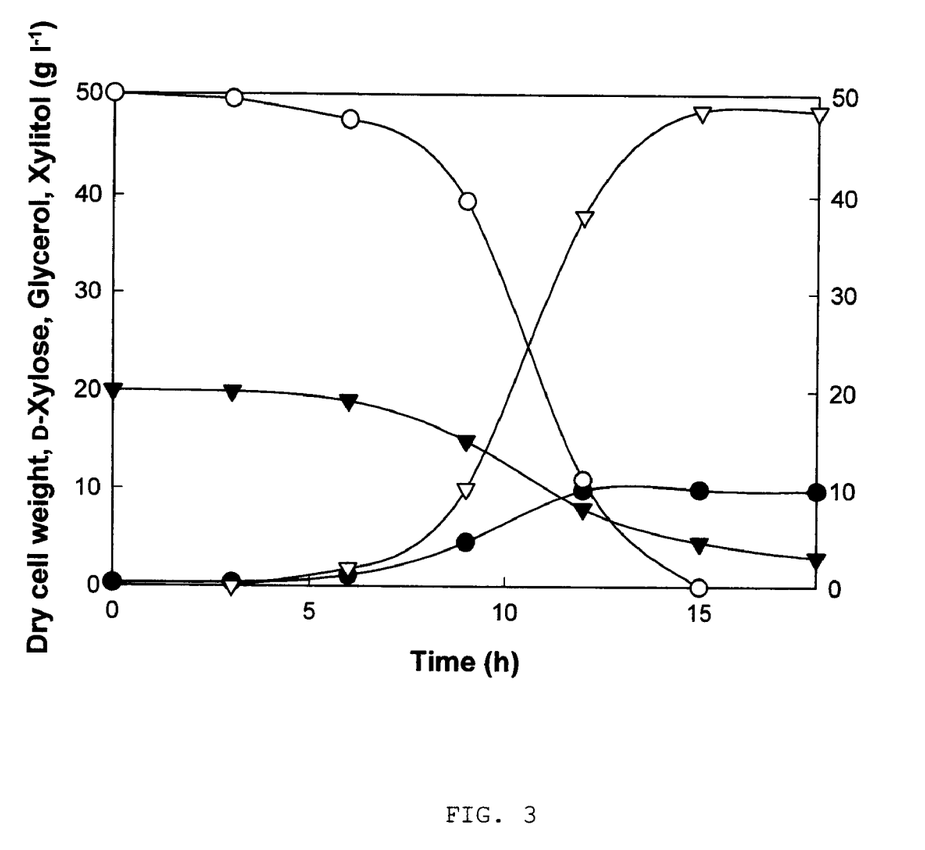
FIG. 3 is a xylitol fermentation profile of xylitol dehydrogenase gene-disrupted mutant of *C. tropicalis* in a 2.5-liter jar fermenter. Glycerol was used as a cosubstrate for initial cell growth and cofactor regeneration. Symbols: ●, dry cell weight; ○, D-xylose; ▼, glycerol; ∇, xylitol

FIG. 3 is a profile of the changes in dry cell weight, D-xylose, glycerol and xylitol concentrations over time when glycerol was used as a sole carbon source. Closed circle (●) indicates dry cell weight, open circle (○) D-xylose concentration, closed inverted triangle (▼) glycerol concentration and open inverted triangle (▽) xylitol concentration, respectively.

The cofactor for reduction of D-xylose to xylitol by xylose reductase was regenerated by the assimilation of glycerol as a sole carbon source. The fermentation was ended at 14 hours and the final xylitol concentration was 48.8 g l$^{-1}$. The xylitol productivity and yield were 3.48 g l$^{-1}$ h$^{-1}$ and 98%, respectively.

Example 6

The Effect of Oxygen Transfer Rate on the Xylitol Production Kinetics

The modified strain, BS-xdh, which was constructed as described in Example 1 was inoculated in 15-ml test tube containing 3 ml of YM medium and incubated using shaking incubator at 30° C. and 200 rpm for 12 hours. 1 ml of the said seed culture was inoculated in 250-ml flask containing 50 ml of YM medium and incubated using shaking incubator at 30° C. and 200 rpm for 12 hours.

Figure 4:
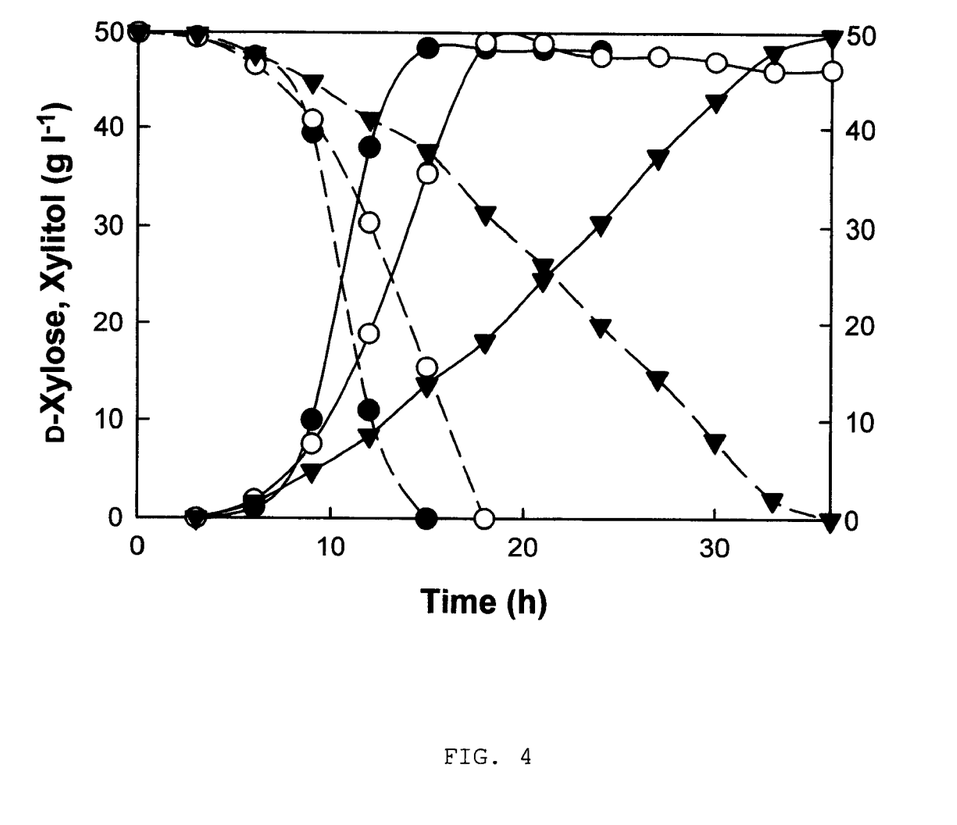
FIG. 4 is a profile showing the effect of the oxygen transfer rate (OTR) on the xylitol production kinetics. Dashed and solid lines indicate the D-xylose and xylitol concentrations, respectively. Symbols: ▼, OTR, 10 mmol $O_2$ $l^{-1}$ $h^{-1}$(300 rpm); ○, OTR, 24 mmol $O_2$ $l^{-1}$ $h^{-1}$(400 rpm); ●, OTR, 42 mmol $O_2$ $l^{-1}$ $h^{-1}$(500 rpm)

The 50 ml of the said seed culture was inoculated in a 2.5-liter jar fermenter (KoBiotech, Korea) containing 1 L of the xylitol production medium supplemented with 20 g l$^{-1}$ glycerol at pH 4.5, and 30° C. The fermentation experiments were performed at agitation speeds of 300, 400, and 500 rpm, 1.0 vol vol$^{-1}$ min$^{-1}$(vvm) of aeration. The oxygen transfer rates (OTR) at 300, 400, and 500 rpm were 10, 24, 42 mmol O$_2$ l$^{-1}$ h$^{-1}$, respectively. Concentration changes of xylitol and D-xylose were analysed with the passage of time under different OTR conditions by the methods described in Example 2 (see: FIG. 4). Dashed and solid lines indicate D-xylose and xylitol concentrations, and closed inverted triangle (▼) indicates OTR, 10 mmol O$_2$ l$^{-1}$ h$^{-1}$(300 rpm), open circle (○) OTR, 24 mmol O$_2$ l$^{-1}$ h$^{-1}$(400 rpm) and closed circle (●) OTR, 42 mmol O$_2$ l$^{-1}$ h$^{-1}$(500 rpm), respectively.

The volumetric productivity of xylitol was dependent on the agitation speed and OTR and varied in the range of from 1.4 to 3.5 g l$^{-1}$ h$^{-1}$, while xylitol yield was not dependent on the agitation speed and OTR and in the range between 97% and 100%. The volumetric productivity was maximal at the agitation speed of 500 rpm and OTR of 42 mmol O$_2$ l$^{-1}$ h$^{-1}$, however it did not decrease so much under a fed-batch culture condition of agitation speed 300 rpm and OTR 42 mmol O$_2$ l$^{-1}$ h$^{-1}$. This indicated that the agitation speed and the OTR affect the glycerol assimilation rate and consequently the xylitol production. When BS-xdh converts D-xylose to xylitol, sufficient oxygen supply is essential for the rapid regeneration of cofactor and results in a high xylitol production rate. This shows that the xylitol productivity by BS-xdh is affected dramatically by the OTR.

Previous studies have found that the xylitol yield and volumetric productivity were maximal with a non-metabolically engineered *Candida parapsilosis* when the dissolved oxygen level was controlled between 0.8% and 1.2% (see: Kim, S. Y, et al., U.S. Pat. No. 5,686,277 (1997)). However, controlling of the dissolved oxygen at the level of 0.8-1.2% was not easy in the industrial scale and, as a result, the xylitol yield was below 70% and productivity could not achieve an economical efficiency. The result shown in this Example 6 has demonstrated that metabolically engineered mutant, BS-xdh, produced xylitol at the almost theoretical yield of 97-100% regardless of the O$_2$ transfer rate. This suggests that the xylitol yield of the mutant resulted from blocking xylose metabolism via disruption of the xylitol dehydrogenase gene, not from a redox imbalance in the cell cytoplasm. In addition, byproducts such as ethanol and glycerol which are synthesized for redox balance in the cytoplasm at oxygen limiting condition were not accumulated in the medium because oxygen was sufficiently supplied into the medium.

Example 7

Xylitol Production Using Fed-Batch Culture (I)

The hemicellulose hydrolysate of corn cob which contains D-xylose as a main constituent is an economically valuable raw material for industrial xylitol manufacturing because it is quite cheaper than pure D-xylose as a precursor of xylitol. In addition, a high concentration of xylitol is also important in the recovery process such as concentration and crystallization. Thus, fed-batch culture was performed to enhance the final xylitol concentration using the hydrolysate of corn cob.

The modified strain, BS-xdh, which was constructed as described in Example 1 was inoculated in 15-ml test tube containing 3 ml of YM medium and incubated using shaking incubator at 30° C. and 200 rpm for 12 hours. 1 ml of the said seed culture was inoculated in 250-ml flask containing 50 ml of YM medium and incubated using shaking incubator at 30° C. and 200 rpm for 12 hours.

50 ml of the seed culture was inoculated in a 2.5-liter jar fermenter (KoBiotech, Korea) containing 1 L of xylitol production medium including 20 g l$^{-1}$ glycerol and cultured at pH 4.5, and 30° C. The corn cob hydrolysate was used to prepare the xylitol production medium (100 g l$^{-1}$ D-xylose, 7 g l$^{-1}$ glucose, 13 g l$^{-1}$ L-arabinose, 30 g l$^{-1}$ glycerol, 10 g l$^{-1}$ yeast extract, 5 g l$^{-1}$ potassium dihydrogenphosphate, and 0.2 g l$^{-1}$ magnesium sulfate heptahydrate). When D-xylose concentration was decreased at the level of 10 g l$^{-1}$, 200 ml of the feeding solution (500 g l$^{-1}$ D-xylose, 35 g l$^{-1}$ glucose, 65 g l$^{-1}$ L-arabinose, 30 g l$^{-1}$ glycerol) was added.

Figure 5:
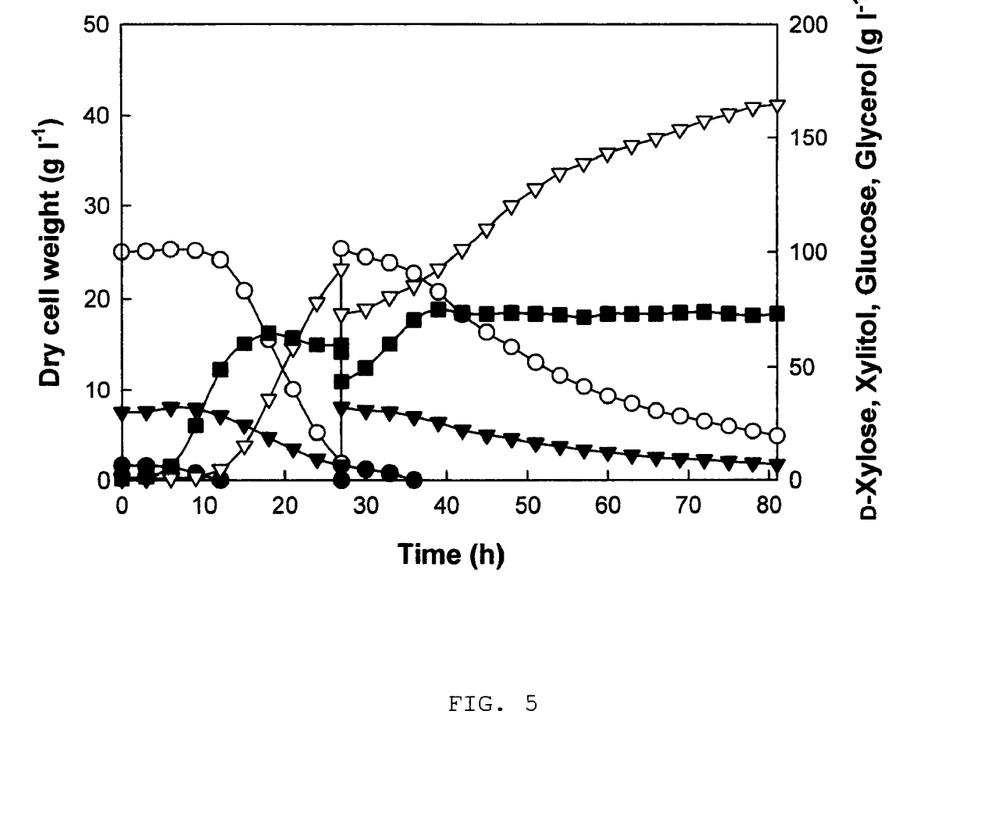
FIG. 5 is a fed-batch culture profile of xylitol dehydrogenase gene-disrupted mutant of *C. tropicalis* in a 2.5-liter jar fermenter. Symbols: ■, dry cell weight; ●, glucose; ○, D-xylose; ▼, glycerol; ∇, xylitol

Dry cell weight and the concentrations of glucose, D-xylose, glycerol and xylitol were analysed with the passage of time by the methods described in Example 2 (see: FIG. 5). Closed square (■) indicates dry cell weight, closed circle (●) glucose concentration, open circle (○) D-xylose concentration closed inverted triangle (▼) glycerol concentration and open inverted triangle (□) xylitol concentration, respectively. As can be seen in FIG. 5, the total amount of consumed D-xylose was 167 g l$^{-1}$ for 81 hours, and final xylitol concentration of 165 g l$^{-1}$ was obtained with 99% xylitol yield from D-xylose.

Example 8

Xylitol Production Using Fed-Batch Culture (II)

The modified strain, BS-xdh, which was constructed as described in Example 1 was inoculated in 15-ml test tube containing 3 ml of YM medium and incubated using shaking incubator at 30° C. and 200 rpm for 12 hours. 1 ml of the said seed culture was inoculated in 250-ml flask containing 50 ml of YM medium and incubated using shaking incubator at 30° C. and 200 rpm for 12 hours.

50 ml of the seed culture was inoculated in a 2.5-liter jar fermenter (KoBiotech, Korea) containing 1 L of xylitol production medium including 20 g l$^{-1}$ glycerol and cultured at pH 4.5, and 30° C. The corn cob hydrolysate was used to prepare the xylitol production medium (50 g l$^{-1}$ D-xylose, 4 g l$^{-1}$ glucose, 7 g l$^{-1}$ L-arabinose, 20 g l$^{-1}$ glycerol, 10 g l$^{-1}$ yeast extract, 5 g l$^{-1}$ potassium dihydrogenphosphate, and 0.2 g l$^{-1}$ magnesium sulfate heptahydrate). When D-xylose concentration was decreased at the level of 10 g l$^{-1}$, 100 ml of the feeding solution (500 g l$^{-1}$ D-xylose, 35 g l$^{-1}$ glucose, 65 g l$^{-1}$ L-arabinose, 30 g l$^{-1}$ glycerol) was added.

Figure 6:
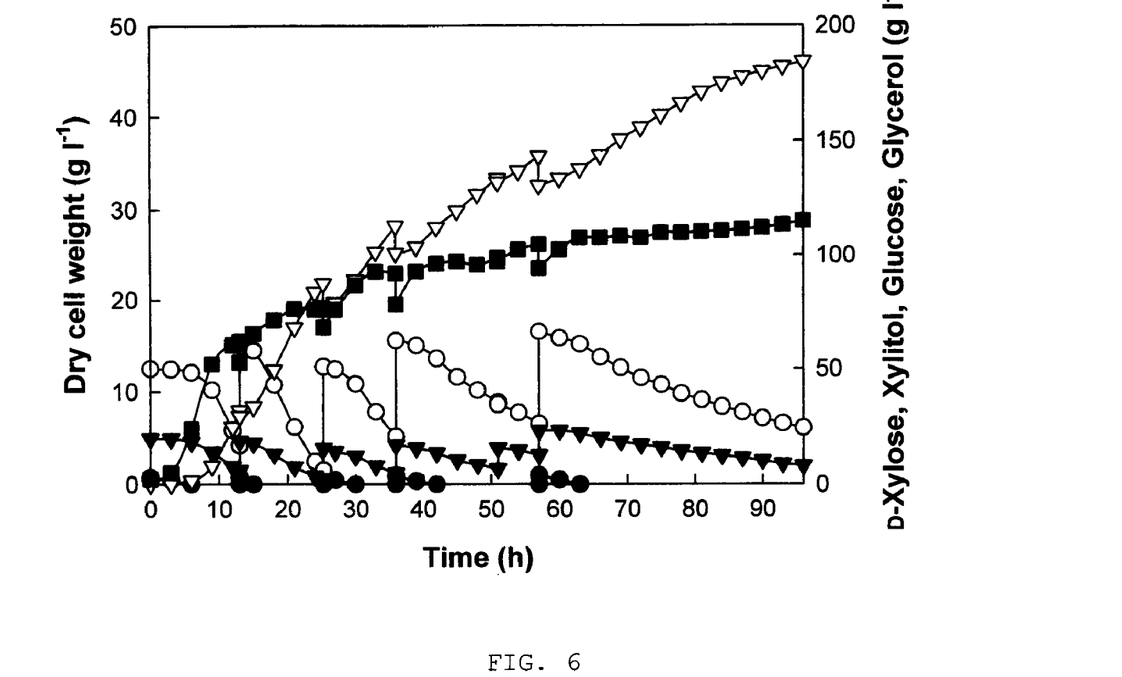
FIG. 6 is a fed-batch culture profile of xylitol dehydrogenase gene-disrupted mutant of *C. tropicalis* in a 2.5-liter jar fermenter. Symbols: ■, dry cell weight; ●, glucose; ○, D-xylose; ▼, glycerol; ∇, xylitol

Dry cell weight and the concentrations of glucose, D-xylose, glycerol and xylitol were analysed with the passage of time by the methods described in Example 2 (see: FIG. 6). Closed square (■) indicates dry cell weight, closed circle (●) glucose concentration, open circle (○) D-xylose concentration closed inverted triangle (▼) glycerol concentration and open inverted triangle (□) xylitol concentration, respectively. As can be seen in FIG. 6, the total amount of consumed D-xylose was 186 g l$^{-1}$ for 96 hours, and final xylitol concentration and xylitol yield were 184 g l$^{-1}$ and 99%, respectively.

What is claimed is:

1. A method for manufacturing xylitol which comprises a step of culturing a xylitol dehydrogenase-deficient mutant of *Candida tropicalis* whose xylitol dehydrogenase expression is disrupted by deletion, substitution or insertion into a part of the xylitol dehydrogenase coding sequence in a medium comprising xylose, a carbon source, a nitrogen source, and trace elements until the xylose contained in the medium is substantially consumed, whereby xylitol is produced.

2. The method for manufacturing xylitol of claim 1 wherein the carbon source comprises glycerol, fructose, galactose, sucrose, mannose, maltose, cellobiose or a mixture thereof.

3. The method for manufacturing xylitol of claim 1 wherein the nitrogen source comprises yeast extract.

4. The method for manufacturing xylitol of claim 1 wherein the trace elements comprise potassium dihydrogenphosphate, magnesium sulfate heptahydrate or a mixture thereof.

5. The method for manufacturing xylitol of claim 1 wherein the xylitol dehydrogenase-deficient mutant is cultured at 20° C. to 40° C.

6. The method for manufacturing xylitol of claim 1 wherein the xylitol dehydrogenase-deficient mutant is cultured in a fed-batch under a condition of agitation speed 300 to 500 rpm and oxygen transfer rate (OTR) 10 mmol $O_2$ $l^{-1}$ $h^{-1}$ to 42 mmol $O_2$ $l^{-1}$ $h^{-1}$.

7. The method for manufacturing xylitol of claim 1 wherein the xylose is added to the medium in a form of hydrolysate of corncob.

* * * * *

UNITED STATES PATENT AND TRADEMARK OFFICE
CERTIFICATE OF CORRECTION

PATENT NO. : 7,745,177 B2  Page 1 of 1
APPLICATION NO. : 11/677685
DATED : June 29, 2010
INVENTOR(S) : Jung-Hoe Kim and Byoung-Sam Ko It is certified that error appears in the above-identified patent and that said Letters Patent is hereby corrected as shown below:

On the Title Page, item (56) Column 2 (Other Publications), line 15, delete "Pichis" and insert
-- Pichia --

Signed and Sealed this

Twenty-third Day of November, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: primer

```
<400> SEQUENCE: 1
aatggtcttg ggtcacgaat cc                                              22

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
gctctgacca agtcgtaggc ttc                                             23

<210> SEQ ID NO 3
<211> LENGTH: 37
<212> TYPE: DNA
<213> ORGANISM: Artificial Sequence
<220> FEATURE:
<223> OTHER INFORMATION: primer

<400> SEQUENCE: 3
ggatccattc tagatgatct ggtttggatt gttggag                              37

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
ggatccatct cgagtcatga gaactaaact agcag                                35
```